US010423757B2

(12) United States Patent
Kruecker et al.

(10) Patent No.: US 10,423,757 B2
(45) Date of Patent: Sep. 24, 2019

(54) SYSTEM AND METHOD FOR PROBABILISTIC ABLATION PLANNING

(75) Inventors: Jochen Kruecker, Washington, DC (US); Sandeep Dalal, Cortlandt Manor, NY (US); Bradford Johns Wood, Potomac, MD (US); Sheng Xu, Rockville, MD (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1180 days.

(21) Appl. No.: 13/885,714

(22) PCT Filed: Nov. 7, 2011

(86) PCT No.: PCT/IB2011/054952
§ 371 (c)(1),
(2), (4) Date: Nov. 8, 2013

(87) PCT Pub. No.: WO2012/066449
PCT Pub. Date: May 24, 2012

(65) Prior Publication Data
US 2014/0058387 A1    Feb. 27, 2014

Related U.S. Application Data

(60) Provisional application No. 61/414,938, filed on Nov. 18, 2010.

(51) Int. Cl.
*A61B 18/18* (2006.01)
*G06F 19/00* (2018.01)
(Continued)

(52) U.S. Cl.
CPC ............ *G06F 19/00* (2013.01); *A61B 18/148* (2013.01); *A61B 34/10* (2016.02); *G16H 50/50* (2018.01);
(Continued)

(58) Field of Classification Search
CPC .... A61B 2018/00577; A61B 2019/504; A61B 19/5225; A61B 18/148; A61B 19/50;
(Continued)

(56) References Cited

U.S. PATENT DOCUMENTS 6,575,969 B1   6/2003  Rittman, III et al.
9,144,461 B2   9/2015  Kruecker et al.
(Continued)

FOREIGN PATENT DOCUMENTS

CN        101859341 A     10/2010
WO        WO200209571      2/2002
(Continued)

OTHER PUBLICATIONS

B.J. Wood et al., "Technologies for Guidance of Radiofrequency Ablation in the Multimodality Interventional Suite of the Future", J. Vasc Interv. Radiol. Jan. 2007; 18(1 Pt 1), pp. 1-26.

*Primary Examiner* — Michael F Peffley
*Assistant Examiner* — Amanda L Zink

(57) ABSTRACT

A system and method for ablation planning includes defining (502) shapes and sizes for one or more ablation volumes based on probability of treatment, and determining (510) a target volume to be treated. A procedure plan is provided (516) by determining a number and location of planned ablations within the target volume using the one or more ablation volumes. A joint probability distribution (520) is determined for at least two planned ablations in the target volume. A final configuration is visualized (530) to determine if plan objectives are met based on a probability of treatment for the target volume.

14 Claims, 5 Drawing Sheets

(51) Int. Cl.
*A61B 18/14* (2006.01)
*A61B 34/10* (2016.01)
*G16H 50/50* (2018.01)
*A61B 18/00* (2006.01)
*A61B 90/00* (2016.01)

(52) U.S. Cl.
CPC ..... *A61B 90/37* (2016.02); *A61B 2018/00577* (2013.01); *A61B 2034/104* (2016.02)

(58) Field of Classification Search
CPC ... A61B 2034/104; A61B 34/10; A61B 90/37; G06F 19/3437
See application file for complete search history.

(56) References Cited

U.S. PATENT DOCUMENTS

| | | | |
|---|---|---|---|
| 9,747,684 | B2 | 8/2017 | Trovato et al. |
| 2006/0200121 | A1 | 9/2006 | Mowery |
| 2008/0234700 | A1 | 9/2008 | Trovato et al. |
| 2009/0136108 | A1 | 5/2009 | Badiei et al. |
| 2009/0318804 | A1* | 12/2009 | Avital ................. A61B 18/02 600/439 |

FOREIGN PATENT DOCUMENTS

| | | |
|---|---|---|
| WO | WO2007129308 | 11/2007 |
| WO | WO2008090484 | 7/2008 |
| WO | WO2010064154 | 6/2010 |

* cited by examiner

SYSTEM AND METHOD FOR PROBABILISTIC ABLATION PLANNING

GOVERNMENT RIGHTS

This invention was made in the performance of a Cooperative Research and Development Agreement with the United States Public Health Service (CRADA No. NCI-NIHCC-01864). The Government of the United States may have certain rights in the invention.

This disclosure relates to medical systems and procedures, and more particularly to systems and methods for more accurately planning ablation regions within a subject.

Ablation procedures such as radiofrequency ablation (RFA) or cryo-ablation are being performed in increasing numbers as an alternative to more invasive surgical procedures. During RFA, an electrode with an un-insulated tip is inserted into a tumor or lesion to be ablated under ultrasound, computed tomography (CT) or magnetic resonance imaging (MRI) guidance. When the electrode is placed, a radiofrequency current is applied to the tip which creates tissue heating and cell death above 60° Celsius. To destroy tumors that are larger than the volume around the needle tip that is heated and destroyed in a single ablation, the needle tip needs to be repeatedly repositioned to ablate different parts of the tumor. The different parts need to partly overlap one another. This process needs to be repeated until the entire tumor is "covered" by the set of ablations, also referred to as a "composite ablation".

Currently, these composite ablations are performed without quantitative or computerized planning and depend on the intuition and experience of the physician. The process of composite ablation planning is difficult, and it has been pointed out that full coverage of a planned treatment volume (PTV) with (smaller) individual ablations generally requires a surprisingly large number of ablations. Thus, there is no guarantee that a "mentally planned" composite ablation actually fully covers the PTV, or that it covers the PTV in an optimal fashion, i.e., with the minimum number of ablations (each ablation taking between 12 and 20 minutes).

In accordance with the present principles, systems and methods for ablation planning include defining probability maps of individual ablations reflecting the spatial extent and variation of the likelihood of successful tissue ablation in the volume surrounding a tip of an ablation probe. Joint ablation probability maps are computed from pluralities of overlapping individual probability maps. The joint maps are used to optimize the planned number and placement of individual ablations such that a target volume is optimally ablated. The optimal plan is used to guide the actual ablation procedure of the target volume. Intra-procedural feedback about the actual location and actual probability map of successful ablations may be used to visualize the progression of the actual procedure and to update the plan as needed.

A system and method for ablation planning includes defining shapes and sizes for one or more ablation volumes based on probability of treatment, and determining a target volume to be treated. A procedure plan is provided by determining a number and location of planned ablations within the target volume using the one or more ablation volumes. A joint probability distribution is determined for at least two planned ablations in the target volume. A final configuration is visualized to determine if plan objectives are met based on a probability of treatment for the target volume.

A method for ablation planning and execution includes developing a treatment plan for treating a target volume including defining shapes and sizes for one or more ablation volumes based on probability of treatment; determining a number and location of planned ablations within the target volume using the one or more ablation volumes; and determining a joint probability distribution for at least two planned ablations in the target volume. An ablation probe is guided to planned ablation locations and the target volume is ablated in accordance with the plan. A probability map is displayed on a display for an executed ablation using a visual effect overlaid on an image of the target volume. The treatment plan is updated in accordance with displayed probabilities.

A system and workstation include a processor and a memory coupled to the processor. The memory stores a probability estimation module and a planning tool. The probability estimation module is configured to define shapes and sizes of ablation volumes in accordance with a treatment probability distribution, determines a joint probability distribution for at least two planned ablations in a target volume, and computes a metric using a spatial representation of a joint probability map and the target volume. The planning tool permits assigning of the ablation volumes to discrete volumes of a target volume in accordance with a plan by determining a number and location of planned ablations within the target volume using the one or more ablation volumes, and optimizes the metric to produce a final configuration of ablation volumes with an associated treatment probability distribution. The treatment probability distribution represents a likelihood of treatment within the ablation volumes.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

Figure 1:
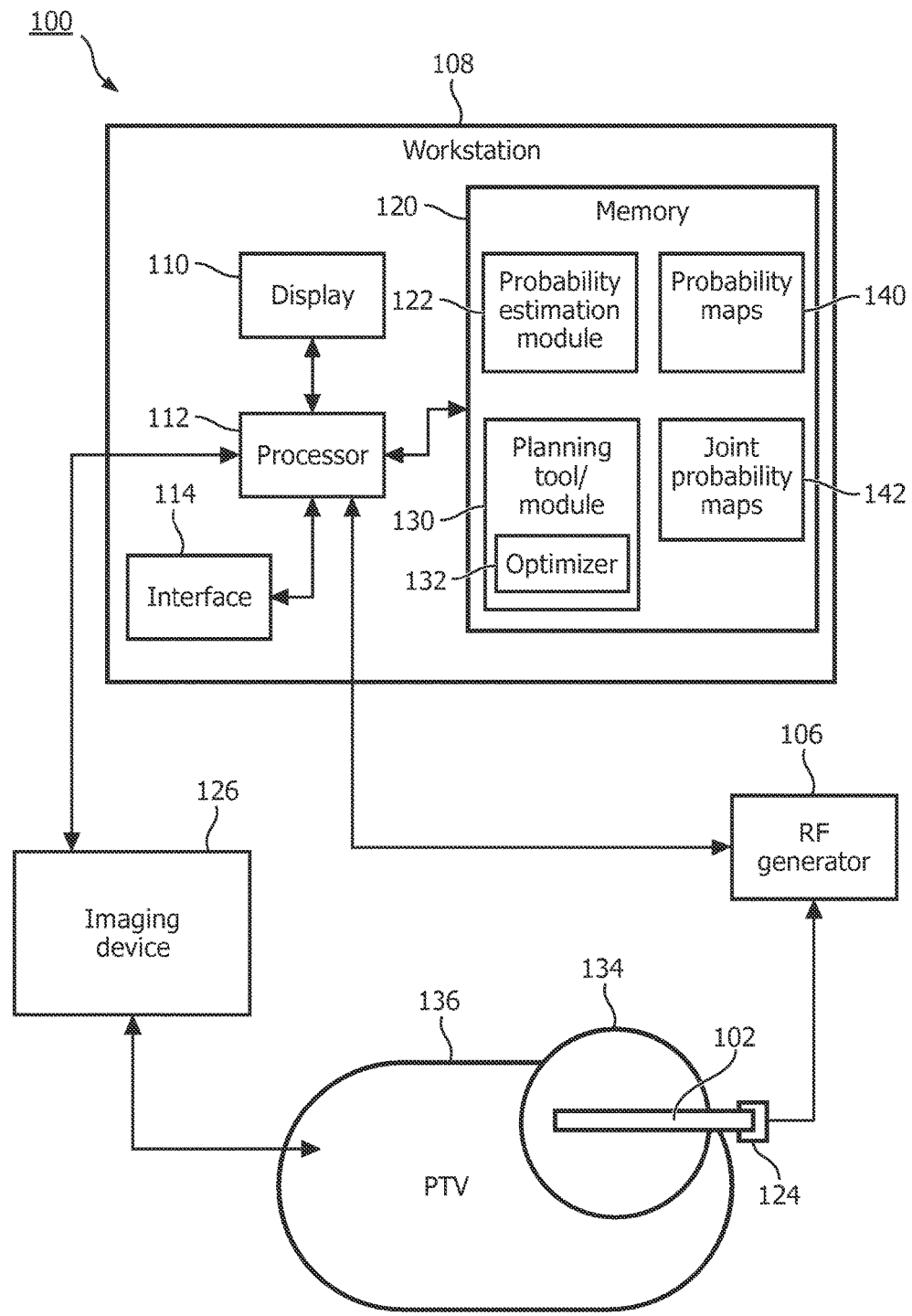
FIG. 1 is a block/flow diagram showing a system/method for ablation planning and implementation of ablation procedures in accordance with one illustrative embodiment.

The present disclosure describes interventional tumor ablation via application of radio frequency energy (RFA), freezing (cryo-ablation) or other methods. Automated planning is introduced that provides for covering a planned treatment volume (PTV) with a minimum number of individual ablations with discrete and well-defined probability distribution shapes and sizes that are independent of one another. The present embodiments recognize that ablations in human tissue may not have well defined, reproducible, discrete shapes and sizes. Instead, the ablation shapes and sizes vary as a function of parameters that may not or cannot be measured accurately during the procedure (e.g., perfusion and micro-structure of the tissue). As a result, individual ablations appear to vary "randomly" and may be better described with a probabilistic approach.

In accordance with the present principles, a probabilistic approach provides a way of introducing synergistic effects between individual ablations, and enables the physician or end user to choose a "confidence level" for eradication of an entire PTV. An advanced ablation planning system is provided that utilizes probabilistic descriptions of ablation shapes and sizes, and optimizes treatment plans based on a probability of coverage of the PTV. It should be understood that the present invention will be described in terms of medical instruments; however, the teachings of the present invention are much broader and are applicable to any instruments employed in treating or analyzing complex biological or mechanical systems. In particular, the present principles are applicable to internal treatment procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Referring now to the drawings in which like numerals represent the same or similar elements and initially to FIG. 1, a system 100 is illustratively shown which defines and/or estimates ablation shapes and sizes using a probabilistic approach. The system 100 includes a radio frequency ablation (RFA) probe 102 (e.g., a single tine or a multi-tine probe). However, probes or other instruments may be employed to perform ablations, such as, cryo-ablation, microwave ablation, etc.

An RF generator 106 provides power to the ablation probe 102 during a procedure. A workstation 108 provides planning/navigation/ablation feedback information to the user using, e.g., a display 110. The workstation 108 may include a computer processor 112, the display 110, a user interface 114 (e.g., mouse, keyboard, etc.) and memory 120 for storing data and software. Memory 120 includes software, which may include a probability estimation module 122 configured to estimate geometry and probabilities associated with the treatment of given regions of a subject. Probabilities may be determined a priori or using user-customized models of the (spatial distribution of) probability of successful ablation around the needle tip for each RFA probe placement. A most likely shape/size of an ablation volume surrounding an ablation site may be computed and may include a probability that a given location has been treated. The probability estimation module 122 is configured to provide or define shapes and sizes of ablation volumes in accordance with a treatment probability distribution. The module 122 may determine a joint probability distribution for at least two planned ablations in a target volume, and compute a metric using a spatial representation of a joint probability map and the target volume.

A spatial tracking system/device 124 may be employed to determine a probe position relative to a medical image provide by an imaging device 126, e.g., an X-ray machine, a computed tomography (CT) imaging device, a magnetic resonance imaging (MRI) device, an ultrasonic (US) imaging device, etc. The spatial tracking system/device 124 may include, for example, a 6 degree-of-freedom electromagnetic (EM) tracking sensor can be placed on the RFA probe as the tracking device 124. In one embodiment, the module 122 collects data such as a position, treatment time, perfusion, etc. to be able to estimate the probability of treatment of this and surrounding areas. A treatment region 134 may be displayed and may be overlaid on an imaging scan showing the probe 102, the treatment region 134 and/or a planned treatment volume (PTV) 136. Spatially correct positions for the probe 102, regions 134 and the PTV 136 may be displayed using the tracking device 124 deployed on the probe 102. Probabilities in and around planned ablation regions 134 may be computed by module 122 along radial directions on parallel equatorial planes to represent a planned (or achieved) ablation shape in the form of probability regions (see FIG. 2). The ablation probability region shape may also be overlaid on a scan or image and the PTV 136 to display the volume to be ablated and nearby voxels inside or around the PTV.

An ablation may show voxels in different probability regions in a particular color, texture or other visibly distinguishing feature. In one example, portions inside the PTV may have a different texture or other effect then portions outside the PTV, e.g., they may have a different color. A residual PTV may be represented and may be displayed to assist in planning for additional ablations during the planning phase.

A planning tool 130 provides assistance in planning the locations of ablations and displays the ablations as probability regions. Planning tool 130 assists in enabling a procedure plan for achieving plan objectives. For example, plan objectives may include a treatment probability of an entire PTV higher than a certain threshold, a treatment probability of healthy tissue being lower than a certain threshold, a minimized volume of healthy tissue treated with a probability higher than a threshold, etc.

The planning tool 130 permits the assignment of the ablation volumes to discrete volumes of a target volume in accordance with the plan by determining a number and location of planned ablations within the target volume using one or more ablation volumes. The planning tool optimizes the metric determined by module 122 to produce a final configuration of ablation volumes with an associated treatment probability distribution. The treatment probability distribution represents, e.g., a likelihood of treatment within the ablation volumes. It should be understood that the planning module and the probability estimation module 122 may be combined, or some or all of the functions may be provided by one or both modules.

The module 122 is capable of computing an achieved composite ablation shape or treatment region based on probability of treatment of each of discrete volumes (e.g., voxels) in individual ablations contributing to the composite ablation shape. The probability may include such factors as ablation duration, probe position, perfusion, etc. In some embodiments, further guidance may come from information gathered from previous procedures and technologies. For example, radiotherapy treatment planning uses quantitative approaches for modeling the impact of radiation treatment on tumor and normal tissue using a probabilistic approach. Tumor Control Probability (TCP) and Normal Tissue Complication Probability (NTCP) for radiotherapy treatment plan evaluations may be employed. TCP represents the probability of successful local tumor control whereas NTCP represents the probability of some defined undesirable effect on the healthy tissue for a planned dose distribution in a radiotherapy treatment plan. Other concepts may include hyperthermia therapy, which employs a thermal dose delivered to tissue. Using knowledge of temperature achieved in a tissue and a time-temperature relationship, an equivalent time exposure at a reference temperature may be calculated. Thermal dose can be used to quantify the probability of a biological effect on tissue to achieve a successful therapeutic response.

Using a mapped volume or other image of an internal region of a subject, the composite ablation region can be visualized on the display 110 by overlaying a joint probability distribution over a planning target volume (PTV) for a lesion or tumor and enabled by the planning module 130. The module 122 computes the probability of positions or voxels in an image to show regions of complete or partial treatment. The probability regions can be overlaid on the PTV so that the clinician or physician can visualize a more accurate version of a treated region.

In one embodiment, module 122 may further provide that a residual PTV is computed and visualized by subtracting completely treated ablated voxels (within a threshold, e.g., 95% probability) inside the original PTV. The computation of the residual PTV during an ablation procedure may be employed as feedback to show regions that still need to be treated.

The ablation planning tool 130 may be stored in memory 120 and may compute an optimal number and placement of ablations to cover the entire PTV or the residual PTV as ablations are performed during the procedure. Manufacturer-specified ideal size and shape of the ablation for planning a RFA procedure may be accounted for in determining the probability distribution for each ablation. The shapes and sizes may be obtained under the assumption of unperfused and perfectly homogeneous tissue. These shapes and sizes may be adjusted based upon information about perfused non-homogeneous tissue. Blood flow in nearby vessels alters the shape of the ablation by cooling the ablation zone locally. If the highest temperature measured is lower than 50° C. then it is unlikely that the tissue around the sensed area has been ablated. System 100 geometrically registers the 3D positions of the tissue regions where the probe 102 is inserted. This permits temperature maps to be determined and included in the computation of probability on the ablation shapes.

Temperature maps can be used to update probability maps. Temperature maps are one way of generating the a priori probability maps for a single ablation, e.g., from finite element modeling simulations, from actual empirical data on phantoms/animal studies, etc.

Ablation planning approaches may model ablations as having a specific size and shape (e.g., ellipsoid with fixed radii a, b, c). With this model, all tissue "inside" the ablation shape is considered fully ablated, i.e., eradicated, and all tissue outside the shape was considered unaffected by the ablation and thus alive. The planning objective was to cover the PTV entirely with the minimum number of copies of the same individual ablation, and provide the location of the individual ablations to the physician.

A mathematical description of the ablations (and the PTV) as having a well-defined, fixed size (with everything inside ablated, but nothing outside ablated) has several disadvantages. These may include: 1) When trying to cover the PTV by placing increasing numbers of ablations, often times there are very small fractions of the PTV (e.g., single voxels) that remain uncovered and thus need placement of additional ablations. Clinically, adding these additional ablations to the treatment may not make sense because of the inherent uncertainty in the individual ablation size, and because of the significant time needed to perform the additional ablation. If an adjacent voxel is considered "definitely covered" by an ablation, then the "uncovered" voxel is also "very likely" to have been ablated and does not warrant the time for an additional ablation. 2) With "fixed" ablation sizes, individual ablations are inherently independent of one another, and it is difficult to model the "synergistic effect" of placing several ablations in close proximity. If a voxel is "outside" all placed ablations, it is considered "uncovered", no matter how many ablations are nearby, and how close the ablations are ("all or nothing" model). In reality, tissue that is heated but not quite destroyed/coagulated by one ablation, is more likely to be destroyed by another adjacent ablation, even if it is not inside the immediate "kill zone" of either ablation. 3) Physicians have an intuitive notion of how many ablations may be needed to cover a PTV in a given patient, based on the physician's experience in other patients, and based on the specific patient's anatomy, physiognomy, etc. With fixed-size ablations, it is difficult to produce an automated plan—or to produce the feedback necessary to create an interactive/semi-automated plan—that also satisfies the physician's intuition. E.g., if a solution that covers all voxels in the PTV appears to use too many ablations, it is difficult to determine which ablations should be eliminated from the plan—and how the remaining ablations should be moved—to optimize the remaining coverage. The number of uncovered voxels is easily computed, but is insufficient to describe the quality of the plan.

In accordance with the present principles, probabilistic ablation models are employed. The probability of coverage for each voxel can be computed or estimated based on a priori knowledge of likely ablation shapes and sizes. These ablation volumes are defined in advance and may be selected for a particular plan. A probability histogram can be generated for the PTV, and the physician can select a confidence level threshold for coverage.

In the planning stage, module 122 may be configured to generate visual feedback to the physician. Visually highlighting areas that are unlikely or less likely to be covered by ablations (e.g. by color-coding according to probability) permits the physician to quickly appreciate where additional ablations could be employed to ensure complete tumor eradication (depending on procedure time constraints, and procedure objective: e.g., curative versus palliative). The probabilistic approach enables customization of the planning based on physician-user preference and experience. While physicians can still employ their own experience regarding minimum/maximum expected ablation sizes, the physicians can also take advantage of computer-assisted planning. The user interface 114 permits user-input of these parameters and thus computer-generated plans that conform to the physician's experience.

Planning tool 130 can create PTV coverage plans (probability maps 140) based on any arbitrarily shaped ablations or building blocks. Module 130 can describe individual ablations in a plurality of ways and not just as "binary" (one/zero=inside/outside the ablation) shapes but shapes with spatially varying probability values of coverage. Module 130 includes an optimizer 132 that uses the probability values from module 122 to create coverage plans with a highest probability of coverage for the PTV 136 (with the least number of ablations). Module 122 can compute a joint probability map 142 of coverage for areas that are covered by more than one ablation. In addition, areas between ablations may have probabilities computed such that gaps or spaces between ablated tissue will be assigned a probability as well. These joint probability regions may be mapped onto an image or video by planning tool 130.

Display 110 shows the (spatially varying) probability of coverage throughout the PTV for any given arrangement of ablations. User interface 114 permits interactive input of parameters describing the spatially varying probability of coverage for individual ablations. For example, interactive inputs may be provided pre-procedure using physician experience/preference or other available information. In addition, intra-procedure inputs may include using feedback obtained, e.g., by imaging, measurement etc. during ablation procedures.

The coverage planning of the PTV is based on spatially varying ablation probabilities as opposed to binary coverage planning, although combination may be employed. The physician-user can customize probability descriptions for individual ablations, and visualize overall probability coverage of the resulting coverage plan. Individual ablations are described as three-dimensional (3D) objects with spatially varying scalar probability values.

Ablation probability maps 140 can be used in the planning stage but also in the execution and feedback stage of an ablation procedure. Different use scenarios are described hereinafter. In a planning stage, the planning tool 130 associates individual ablation zones with a fixed individual probability map 140, which is pre-determined or user-specified. Joint probabilities 142 of ablation can be computed by module 122 for any potential configuration of (one or several overlapping) individual planned ablations. An ablation plan is created using planning tool 130 by calculating metrics derived from a pose of the joint probability map 142 relative to the PTV 136, and by modifying the ablation configuration (manually or automatically) until the metric is optimized using optimizer 132. In one embodiment, regions near the PTV 136, e.g., corresponding to certain anatomical features in the medical image, may be identified that modify the joint probability map 142 to reflect local tissue cooling via major blood vessels, etc.

In one embodiment, execution of the ablation plan may be conducted without feedback. The plan can be used to guide a procedure by visualizing the final configuration of individual ablations and/or the joint probability map 142 relative to a medical image. Conventional image guidance methods may be employed to execute the procedure according to the plan, or the plan geometry can be sent to a guidance system (e.g., (electromagnetic or other) to provide needle guidance for each individual ablation. No information about the actual positions, orientations, sizes, or probabilities of ablations needs to be obtained in this embodiment.

In another embodiment, execution of the ablation plan is performed with position/orientation feedback. During procedure execution, an actual position and orientation of the ablation probe or needle 102 relative to the medical image can be determined during each individual ablation using intra-procedural medical imaging, intra-procedural spatial tracking of the ablation needle, etc. For each such individual executed ablation position, the assumed individual probability map 140 (e.g., the same as the one used for pre-procedure planning) can be mapped to the medical image and visualized, thus building up—ablation by ablation—an executed joint probability map 142, which can help the physician assess whether the PTV 136 was actually ablated appropriately. Similar to the planning phase, in one embodiment, regions near the PTV 136 corresponding to certain anatomical features in the medical image may be identified that modify the executed joint probability map 142 to reflect local tissue cooling via major blood vessels, etc.

In yet another embodiment, execution of the ablation plan is performed with position/orientation and size or probability feedback. In addition to the feedback described above, medical imaging or other means can be used to determine or estimate an actual size or a probability map (140) of actual, individual, executed ablations (e.g., modifying the assumed individual probability maps during the planning phase). These modified maps can be used to build up and visualize an executed joint probability map 142 (again without or with consideration of regions near the PTV 136 that may modify the executed joint probability of ablation).

In still another embodiment, execution of the ablation plan is performed with feedback and iterative plan updates. After each executed ablation and update of the executed joint probability map 142, that map 142 can be employed to update (manually or automatically) the procedure plan, in the event that a deviation has occurred between a planned individual ablation probability map 140 and the corresponding executed ablation probability map 142. This ensures that an improved or an optimal plan is provided for the remainder of the procedure after each actual ablation. This plan update can use the same metrics and same calculation of joint probabilities as in the initial planning phase. The only difference in the (manual or automatic) optimization (132) is that one or several individual probability maps 140 (e.g., the executed ones) will be in a fixed location (as confirmed using feedback), while the location/orientation of others (the planned or yet to be executed ones) can still be modified to optimize the overall plan.

Figure 2:
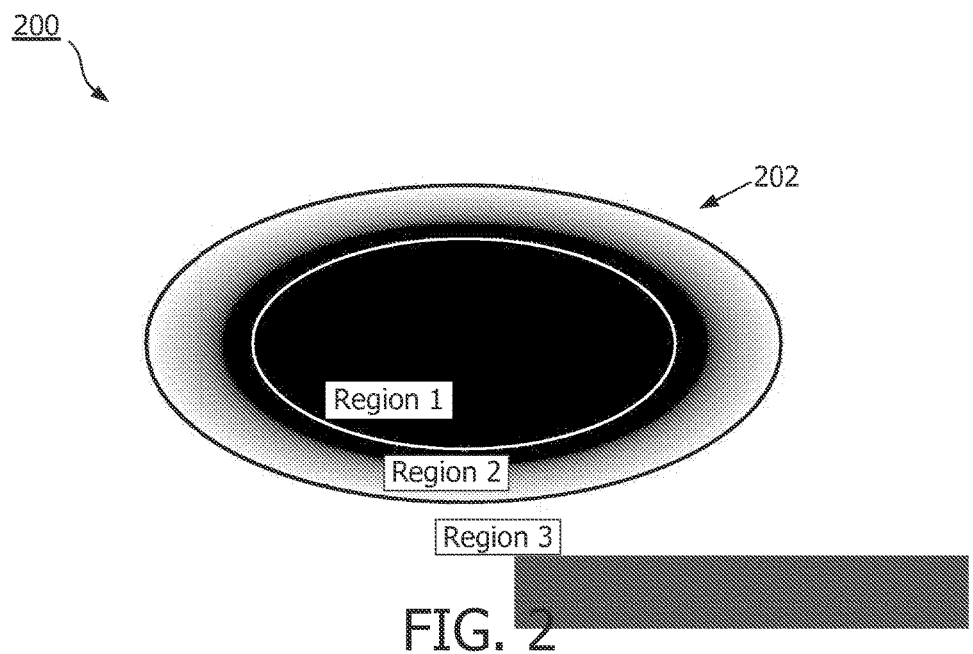
FIG. 2 is a diagram showing an ablation volume having regions of different treatment probability in accordance with one illustrative embodiment.

Referring to FIG. 2, three regions 1, 2 and 3 are illustratively shown for an ablation volume. One embodiment includes a discretized representation of the ablation volume as a 3D array $A_{ijk}$ having values between 0 (definitely not ablated, 0% probability) and 1.0 (definitely ablated, 100% probability). The three array dimensions correspond to the x, y, and z dimensions of the ablation, and an arbitrarily defined voxel size (e.g., 1 $mm^3$) provides the correspondence between voxel index in the array and physical location in the ablation zone.

In FIG. 2, a diagram 200 shows an illustrative probability distribution for an individual ablation volume 202. In this case, the ablation volume 202 includes three different regions, one region is "definitely ablated" (Region 1: all voxels associated with probability 1 in this example), one that is "potentially ablated" (Region 2: voxel values with associated probability between 0 and 1) and one that is "definitely not ablated" (Region 3: voxels associated with probability 0 in this example, which includes all locations outside Regions 1 and 2, and regions outside the voxel array). Ablation probability for a given voxel may also be termed as the voxel value for purpose of this disclosure. Region 1 may employ a simple 3D geometric shape, such as a sphere or an ellipsoid (i.e., all voxels inside that shape have voxel value 1). Region 2 may employ voxel values, which vary from 1 to 0 with increasing spatial distance (up to a maximum distance $r_{max}$, the isotropic "uncertainty margin" around the definitely ablated Region 1 from the border of Region 1). The voxel values in Region 2 may be given by $f_2(x/r_{max})$, where x is the distance from the border of Region 1, $f_2(0)=1$, and $f_2(1)=0$. Both shape of the function $f_2$ and $r_{max}$ can be determined experimentally, computationally (e.g., using finite element simulations) or as user-input based on user experience.

Another advantageous description of Region 2 is that of an ellipsoidal shell. This may include outer radii $rx_{max}$, $ry_{max}$, $rz_{max}$ beyond which the ablation probability is 0, and inner radii $rx_{min}$, $ry_{min}$, $rz_{min}$ which describe the boundary with Region 1. In this implementation, the differences $rx_{max}-rx_{min}$, $ry_{max}-ry_{min}$, $rz_{max}-rz_{min}$ describe the non-isotropic "uncertainty margin" around Region 1. Probabilities in Region 2 are again advantageously described by a function $f_2(s)$ with $f_2(0)=1$, $f_2(1)=0$ and parameterization $E(s)$ of an ellipsoidal surface such that $E(0)$ is the boundary of Region 1, and $E(1)$ is the outer boundary of Region 2, e.g., $$E(s) = \left\{ x, y, z \middle| \frac{x^2}{(rx_{min} + s(rx_{max} - rx_{min}))^2} + \frac{y^2}{(ry_{min} + s(ry_{max} - ry_{min}))^2} + \frac{z^2}{(rz_{min} + s(rz_{max} - rz_{min}))^2} = \right.$$

such that for each spatial location (x, y, z) in Region 2, the parameter $s_0$ can be found with $(x, y, z) \in E(s_0)$, and the ablation probability/voxel value at (x, y, z) is given by $f_2(s_0)$.

The function $f_2(x)$ is advantageously described as a function that decreases continuously from $f_2(0)=1$ to $f_2(1)=0$. E.g., the linear $f_2(x)=1-x$ for $x \in [0, 1]$, the sinusoidal $f_2(x)=0.5*(1-\sin((x-0.5)*\pi))$ for $x \in [0,1]$ or other specific function to be used are advantageously selected by the physician-user using the user interface (114) that visualizes the shape of the function.

For planning, visualization and optimization of the treatment plan, a function $q_n(p_1, p_2, \ldots p_n)$ can be defined determining the "synergistic effect" of ablations in locations where more than one ablation overlaps. One advantageous implementation of $q_n$ defines a joint probability of n independent random events, each having probability of occurrence $p_n$, recursively described as:

$$q_n \begin{cases} \min(1, q_{n-1} + p_n(1 - q_{n-1})) & \text{for } n > 0 \\ 0 & \text{for } n = 0 \end{cases}$$

Figure 3:
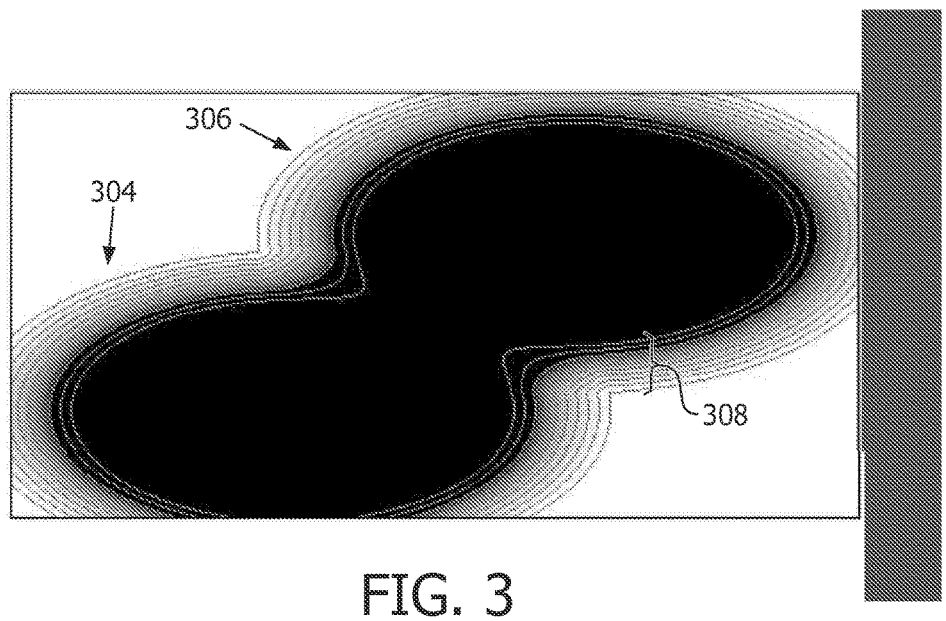
FIG. 3 is a diagram showing two ablation volumes having regions of different treatment probability including cumulative treatment effects in accordance with another illustrative embodiment.
Figure 4:
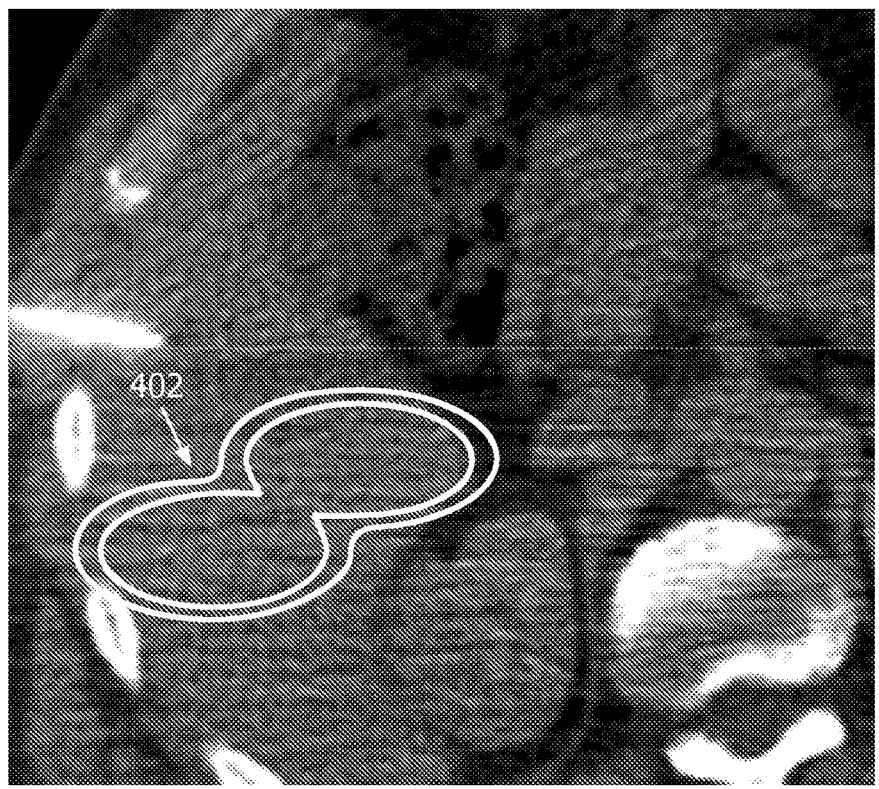
FIG. 4 is a diagram showing two ablation volumes having regions of different treatment probability overlaid on an image of a target volume in a subject in accordance with another illustrative embodiment.

Referring to FIG. 3, a visualization, for a plan created with probabilistic ablation descriptions, is illustratively shown. FIG. 3 shows a visualization (in 2D for simplicity) of two partly overlapping ellipsoidal ablations 304 and 306 with a linear $f_2$, and contour lines 308 in Region 2 showing different probability regions. As each new ablation is added to a plan, a probability region is computed, and its "synergistic effect" is determined. One advantageous implementation is a color-coded overlay 402 of the values of $q_n$ calculated for each voxel, superimposed on a medical image of the treatment area as depicted in FIG. 4. Another advantageous implementation includes the color-coded overlay according to a finite set of threshold levels of $q_n$, e.g., one color for areas with $q_n>0.95$ (most likely ablated), another color for areas with $0.5 \leq q_n \leq 0.95$ (likely ablated, but possibly under-treated), and a third color (or no color) for $q_n<0.5$ (unlikely to be ablated). A greater number of regions may also be employed. Another advantageous implementation permits variable alpha-blending, controlled by the physician-user, of the ablation overlay to show more or less of the underlying medical image.

For automated optimization of a treatment plan, i.e., optimization of the number and placement of individual ablations covering the PTV, a cost function may be defined to be minimized. One advantageous implementation of the cost function is the fraction of the PTV volume for which $q_n$ is below a threshold (e.g. $q_n<0.9$). Another advantageous implementation of the cost function is the sum or integral of the PTV, weighted by a measure of the probability of ablation failure (e.g., $1-q_n$) in each location. In yet another implementation, the physician-user can specify various target probability levels that are to be achieved for different regions of the PTV, e.g., a level of 1.0 for the visible margins of the tumor, a level of 0.9 for a boundary region up to 5 mm from the visible tumor, and a level of 0.5 for a boundary region between 5 mm and 10 mm from the visible tumor. Color-coded visualization can be employed to highlight where these target levels are met, for the given manual or automated plan. In addition, automated optimization, jointly or sequentially can aim to satisfy all target levels.

In another implementation, an anatomical structure that reduces the probability of successful ablation in the structure's vicinity (such as a blood vessel cooling the surrounding tissue) can be segmented and accounted for in the visualization and planning Blood vessels can be approximated locally as cylindrical structures, reducing the probability of ablation by a factor g(r) depending on the distance r from the cylinder, where g(r) can be determined computationally (e.g., with finite element simulations), experimentally, or heuristically (with user-input).

Figure 5:
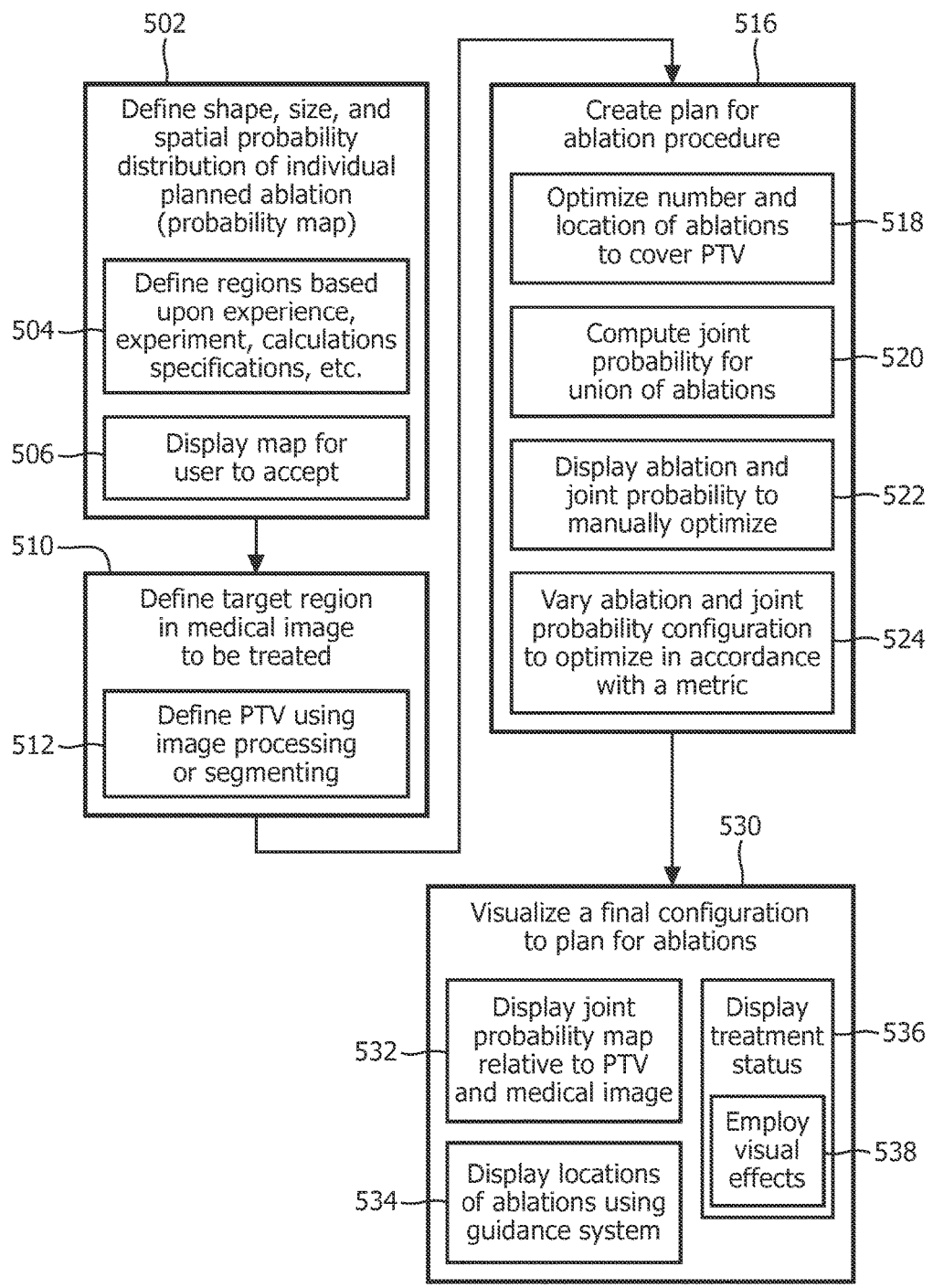
FIG. 5 is a block/flow diagram showing a system/method for planning ablations using probability distributions in accordance with one illustrative embodiment.

Referring to FIG. 5, a block/flow diagram shows a system/method for planning an ablation procedure in accordance with one embodiment. In block 502, shape, size, and spatial probability distribution of individual planned ablations ("individual ablation probability map" or simply "probability map") are defined. In block 504, the probability maps may be pre-defined based on prior experiments, calculations, simulations, estimations, or user-defined based on individual user experience/preference. This may include accounting for perfusion and other characteristics of the area to be treated. In block 506, the individual ablation probability map(s) may be visualized or displayed for the user to accept or modify.

In block 510, in a medical image (CT, MRI, X-ray, etc.), a target region (PTV) to be treated may be defined. In block 512, the PTV may be defined automatically using image processing methods, or defined manually by the user, by "segmenting" a PTV in the image.

In block 516, a planning process is performed to create a plan for an ablation procedure. In block 518, the plan optimizes a number and/or location and orientation of one or several individual ablations such that a planned union of individual ablations optimally covers the PTV. For each potential configuration of individual ablations, a spatially varying joint probability of ablation for the entire region covered by the union of ablations is computed ("joint probability map") in block 520. A composition rule can be expressed (as in the formula for $q_n$) when multiple probabilistic ablations cover a voxel. An effective probability of being ablated is determined for the voxel for a union of ablations.

In block 522, manual optimization may include providing a visualization of each potential configuration of ablations and joint probabilities. A user interface may be employed to interactively modify the configuration until the configuration optimally covers the PTV. In block 524, automatic optimization may include providing optimization algorithms (e.g., cost functions) to vary the individual ablation configuration until a metric derived from the joint probability map is optimized. Metrics may include a probability threshold, PTV coverage, least number of ablations, etc.

In block 530, a final configuration is displayed and employed as a plan for executing the individual ablations. In block 532, a visualization of the final configuration may include the joint probability map relative to the medical image and PTV. In block 534, a visualization of the final configuration may include markers or elements of a guidance system to provide the location coordinates of the individual ablations in the configuration as "targets" for individual ablation needle placements.

In the visualization, regions may be displayed as treated, untreated and transitional, where transitions are between the treated and untreated probability regions. In block 536, the treatment status may be displayed on a display relative to an image of the targets. In block 538, a color-coded (or other visual effect) probability distribution map may be displayed showing the treatment status of the ablation volume is overlaid on/in a three-dimensional image of a subject. The treatment status of the voxels may be displayed by employing a visual effect to represent the probability that the voxel has been treated.

Figure 6:
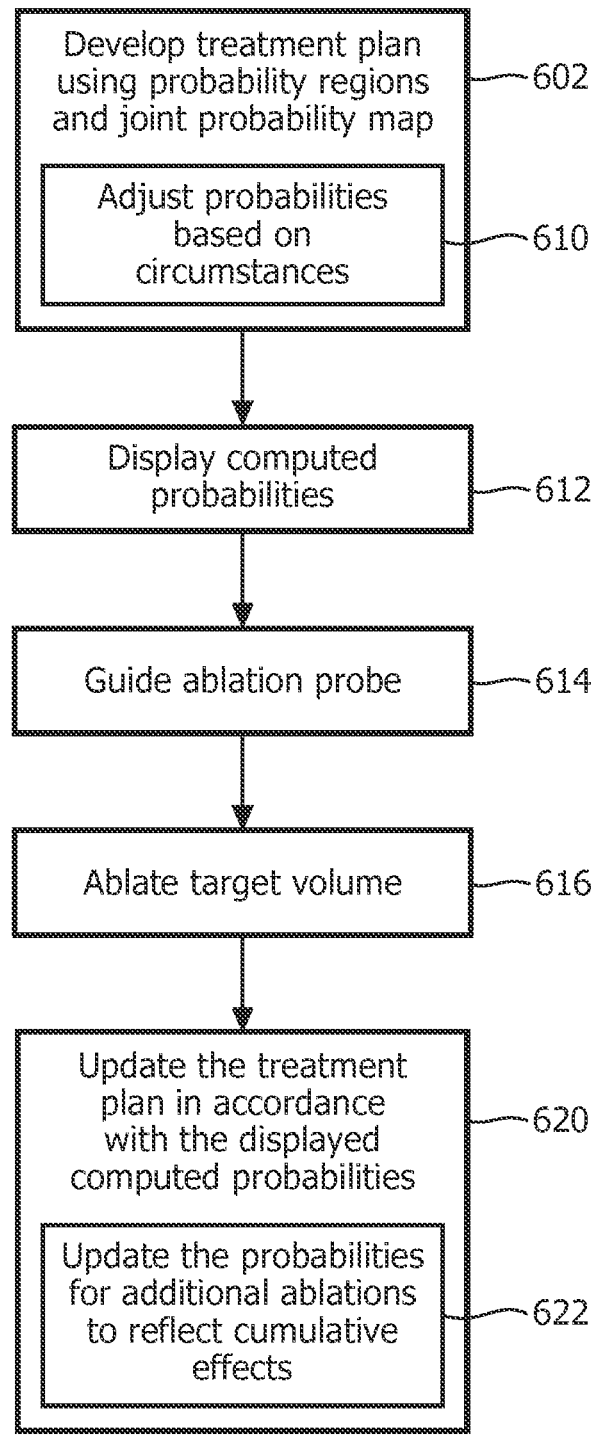
FIG. 6 is another block/flow diagram showing a system/method for planning and performing ablations using probability distributions in accordance with another illustrative embodiment.

Referring to FIG. 6, a block/flow diagram shows a system/method for performing an ablation procedure in accordance with another embodiment. In block 602, a treatment plan is developed for treating a target volume as described in FIG. 5. This includes computing a probability for one or more ablation regions. The regions may include discrete volumes of a target volume which are to be treated by multiple ablations. A probabilistic shape of an ablation volume may be determined based upon one of a physician's experience, experimentation, manufacturer specifications for an ablation probe, etc. A joint probability map of overlapping ablation sites is also computed.

In block 610, the probability may be adjusted based upon specific instances or criteria, for example, blood or fluid perfusion in the target volume may be considered. Blood or other flow models may be employed to adjust the probabilities. These adjustments may be local to a portion of an ablated area closest to the blood vessels. In addition, other adjustments to probability may be made for other effects that would impact the probability that an ablated volume is treated.

In block 612, the probability may be displayed in a display using a visual effect overlaid on an image of the target volume. The visual effect may include colors displayed to represent different probabilities of treatment in the image of the target volume.

In block 614, an ablation probe is guided to the target volume to perform ablation according to the plan. In block 616, the target volume is ablated in accordance with the plan. In block 618, the treatment plan may be updated in accordance with recomputed probabilities to determine a more accurate probability map. This may include displaying a visual effect to reflect the probabilities in a display image. In this way, the user can evaluate whether a position was treated and may determine a best position for a next ablation.

In block 620, the probabilities may be updated in accordance with additional ablations to reflect cumulative effects of multiple ablations. These updates are preferably displayed visually on a display so that the user can determine a location for a next ablation without unnecessarily ablating areas that have already been treated or, due to the accumulated effects in nearby areas, have a high probability of being treated already.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for systems and methods for probabilistic ablation planning (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A workstation, comprising:
a processor; and
a memory coupled to the processor,
the memory storing a probability estimation module and a planning tool,
wherein the probability estimation module defines shapes and sizes of ablation volumes in accordance with a treatment probability distribution representing likelihood of complete treatment by ablation within each of the ablation volumes, determines a joint probability distribution for at least two planned ablations in a target volume, and computes a metric using a spatial representation of a joint probability map and the target volume, and
wherein the planning tool assigns the ablation volumes to discrete volumes of the target volume in accordance with a plan by determining a number and location of planned ablations within the target volume using the ablation volumes, and optimizes the metric to produce a final configuration of ablation volumes with an associated treatment probability distribution having spatially varying treatment probabilities within each of the ablation volumes.

2. The workstation as recited in claim 1, further comprising a display for displaying treatment probabilities of the treatment probability relative to an image of the target volume.

3. The workstation as recited in claim 2, wherein the treatment probabilities are included a color-coded probability distribution map showing a treatment status of the ablation volumes in a three-dimensional image of a subject.

4. The workstation as recited in claim 1, wherein the probability estimation module is configured to determine size and shape of ablation volumes based upon one of physician's experience, simulation, experimentation and manufacturer specifications for an ablation probe.

5. The workstation as recited in claim 1, wherein the probability estimation module is configured to update the treatment probability distribution in accordance with additional ablations to reflect cumulative effects of multiple ablations.

6. The workstation as recited in claim 1, wherein the target volume includes a planned target volume (PTV).

7. The workstation as recited in claim 1, wherein the planning tool is configured to generate the final configuration on a display to determine if plan objectives are met based on treatment probabilities for the target volume.

8. The workstation as recited in claim 1, wherein the probability estimation module is configured to adjust the treatment probability distribution based upon at least perfusion in the target volume.

9. A system, comprising:
a workstation including a processor and a memory coupled to the processor, the memory storing a probability estimation module and a planning tool, wherein the probability estimation module is configured to define shapes and sizes of ablation volumes in accordance with a treatment probability distribution representing likelihood of complete treatment by ablation within each of the ablation volumes, determines a joint probability distribution for at least two planned ablations in a target volume, and computes a metric using a spatial representation of a joint probability map and the target volume, and wherein the planning tool permits assigning of the ablation volumes to discrete volumes of a target volume in accordance with a plan by determining a number and location of planned ablations within the target volume using the ablation volumes, and optimizes the metric to produce a final configuration of ablation volumes with an associated treatment probability distribution having spatially varying treatment probabilities within each of the ablation volumes;
an ablation probe configured to ablate tissue in the target volume; and
a display configured to display an image of the target volume with an overlay showing probability regions over the image of the target volume.

10. The system as recited in claim 9, wherein the treatment probabilities include a color-coded probability distribution map showing a treatment status of the ablation volumes in a three-dimensional image of a subject.

11. The system as recited in claim 9, wherein the probability estimation module determines size and shape of ablation volumes based upon one of physician's experience, simulation, experimentation and manufacturer specifications for an ablation probe.

12. The system as recited in claim 9, wherein the probability estimation module is configured to update the treatment probability distribution in accordance with additional ablations to reflect cumulative effects of multiple ablations.

13. The system as recited in claim 9, wherein the planning tool is configured to generate the final configuration on a display to determine if plan objectives are met based on the treatment probabilities for the target volume.

14. The system as recited in claim 9, wherein the probability estimation module is configured to adjust the treatment probability distribution based upon at least perfusion in the target volume.

* * * * *